United States Patent
Cinader, Jr. et al.

(10) Patent No.: US 7,217,124 B2
(45) Date of Patent: May 15, 2007

(54) ORTHODONTIC BRACKETS INCLUDING ONE PART OF AN AT LEAST TWO-PART ADHESIVE ON THE BASE OF THE BRACKET

(75) Inventors: David K. Cinader, Jr., Yorba Linda, CA (US); Joan V. Brennan, Sierra Madre, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 919 days.

(21) Appl. No.: 10/126,019

(22) Filed: Apr. 18, 2002

(65) Prior Publication Data

US 2003/0198913 A1    Oct. 23, 2003

(51) Int. Cl.
*A61C 3/00* (2006.01)
(52) U.S. Cl. .......................................................... 433/9
(58) Field of Classification Search ............... 433/9, 433/8, 10, 11, 12, 13, 14, 15, 16, 17, 24
See application file for complete search history.

(56) References Cited

U.S. PATENT DOCUMENTS

| | | | |
|---|---|---|---|
| 3,250,003 A | 5/1966 | Collito | |
| 3,655,605 A | 4/1972 | Smith | |
| 3,797,115 A | 3/1974 | Silverman et al. | |
| 3,814,717 A | 6/1974 | Wilson et al. | |
| 4,143,018 A | 3/1979 | Crisp et al. | |
| 4,179,812 A | 12/1979 | White | |
| 4,180,911 A * | 1/1980 | Bullock | 433/9 |
| 4,204,325 A * | 5/1980 | Kaelble | 433/9 |
| 4,209,434 A | 6/1980 | Wilson et al. | |
| 4,360,605 A | 11/1982 | Schmitt et al. | |
| 4,376,835 A | 3/1983 | Schmitt et al. | |
| 4,503,169 A | 3/1985 | Randklev | |
| 4,533,422 A * | 8/1985 | Litke | 156/307.3 |
| 4,695,251 A | 9/1987 | Randklev | |
| 4,948,367 A | 8/1990 | Haas | |
| 4,978,007 A | 12/1990 | Jacobs et al. | |
| 5,015,180 A * | 5/1991 | Randklev | 433/9 |
| 5,147,202 A | 9/1992 | Masuhara et al. | |
| 5,172,809 A | 12/1992 | Jacobs et al. | |
| 5,183,403 A | 2/1993 | Masuhara et al. | |
| 5,219,283 A | 6/1993 | Farzin-Nia et al. | |
| 5,221,202 A | 6/1993 | James | |

(Continued)

FOREIGN PATENT DOCUMENTS

WO    WO 95/25477    9/1995

(Continued)

OTHER PUBLICATIONS

Cabot Corporation Product Information Sheet, "Cab-O-Sil M-5 Untreated Fumed Silica," Cabot Corporation, Tuscola, IL, 2 pages (2001).

(Continued)

*Primary Examiner*—John J Wilson
(74) *Attorney, Agent, or Firm*—James D. Christoff

(57) ABSTRACT

Articles including an orthodontic bracket having a base for bonding the bracket to a tooth are disclosed. A first part of an at least two-part adhesive is on the base of the bracket and a release substrate is in contact with the adhesive.

37 Claims, 1 Drawing Sheet

U.S. PATENT DOCUMENTS

| | | | |
|---|---|---|---|
| 5,295,824 | A | 3/1994 | Wong |
| 5,328,363 | A | 7/1994 | Chester et al. |
| 5,332,429 | A | 7/1994 | Mitra et al. |
| 5,354,199 | A | 10/1994 | Jacobs et al. |
| 5,429,229 | A | 7/1995 | Chester et al. |
| 5,538,129 | A | 7/1996 | Chester et al. |
| 5,552,177 | A | 9/1996 | Jacobs et al. |
| 5,558,516 | A | 9/1996 | Horn et al. |
| 5,575,645 | A | 11/1996 | Jacobs et al. |
| 5,593,303 | A | 1/1997 | Cohen et al. |
| 5,810,584 | A | 9/1998 | Wong |
| 5,827,058 | A | 10/1998 | Kelly et al. |
| 5,890,892 | A | 4/1999 | Lemchen |
| 5,971,754 | A * | 10/1999 | Sondhi et al. ............... 433/24 |
| 6,050,815 | A | 4/2000 | Adam et al. |
| 6,089,861 | A | 7/2000 | Kelly et al. |
| 6,089,868 | A | 7/2000 | Jordan et al. |
| 6,126,922 | A | 10/2000 | Rozzi et al. |
| 6,174,935 | B1 * | 1/2001 | Matsunae et al. ........... 523/118 |
| 6,183,249 | B1 * | 2/2001 | Brennan et al. ............... 433/9 |
| 6,207,077 | B1 * | 3/2001 | Burnell-Jones ........ 252/301.36 |
| 6,213,767 | B1 | 4/2001 | Dixon et al. |
| 6,350,119 | B1 | 2/2002 | Jordan et al. |

FOREIGN PATENT DOCUMENTS

| | | |
|---|---|---|
| WO | WO 00/69393 | 11/2000 |

OTHER PUBLICATIONS

Cabot Corporation Product Information Sheet, "Cab-O-Sil TS-720 Treated Fumed Silica," Cabot Corporation, Tuscola, IL, 2 pages (2001).

Chung et al., "Fluoride release and cariostatic ability of a compomer and a resin-modified glass ionomer cement used for orthodontic bonding," *J. Dent.*, vol. 26, Title page, Publication page, Table of Contents, and pp. 533-538 (1998).

Liddell et al., "Yield stress measurements with the vane," *J. Non-Newtonian Fluid Mechanics,* vol. 63, Publication page, Table of Contents, and pp. 235-261 (1996).

Macosko, "Rheology Principles, Measurements, and Applications," VCH Publishers, Inc., New York, p. 92 (1994).

Kirk-Othmer Encyclopedia of Chemical Technology, 4$^{th}$ Ed., vol. 21, Title page, Publication page, Table of Contents, and pp. 977-1032 (1997).

Sartomer Product Bulletin, "SR-348 Ethoxylated (2) Bisphenol A Dimethacrylate," Sartomer Company, Exton, PA, 1 page (Dec. 2001).

3M Company Material Safety Data Sheet, "3M Unitek Etching Liquid (704-037)," 3M Company, St. Paul, MN, 6 pages (May 7, 2001).

3M Company Material Safety Data Sheet, "3M Unitek Unite Adhesive (704-038, 704-048)," 3M Company, St. Paul, MN, 6 pages (May 21, 2001).

3M Company Material Safety Data Sheet, "3M Unitek Unite No-Mix Adhesive Kit (712-011); Unite Adhesive Syringe Kit (712-012, 712-015)," 3M Company, St. Paul, MN, 1 page (Aug. 22, 2001).

3M Company Material Safety Data Sheet, "3M Unitek Unite Primer (704-055)," 3M Company, St. Paul, MN, 6 pages (Aug. 22, 2001).

3M Company Material Safety Data Sheet, "Unite™ No-Mix Adhesive Kit (GP) (59334, 59001-05, 58513)," 3M Company, St. Paul, MN, 1 page (Mar. 3, 1997).

3M Unitek Product Information Instruction Sheet, "Unite™ Bonding Adhesive For Bonding Metal, Plastic, or Ceramic Brackets," 3M Unitek, Dental Products Division, Monrovia, CA, 1 page (2000).

3M Unitek Product Information Instruction Sheet, "3M Unitek Unite™ Bonding Adhesive," 3M Unitek, Dental Products Division, Monrovia, CA, 2 pages (2000).

Unimin Canada Ltd. Material Safety Data Sheet, "TAMSIL (R), IMSIL (R), and CERASIL (R)—various grades Microcrystalline Silica, Silicon Dioxide," Unimin Canada Ltd., Ontario, Canada (2001).

\* cited by examiner

ORTHODONTIC BRACKETS INCLUDING ONE PART OF AN AT LEAST TWO-PART ADHESIVE ON THE BASE OF THE BRACKET

BACKGROUND

Orthodontic treatment involves movement of malpositioned teeth to orthodontically correct positions. Tiny orthodontic appliances known as brackets are connected to exterior surfaces of the patient's teeth, and an archwire is placed in a slot of each bracket. The archwire forms a track to guide movement of the teeth to desired positions for correct occlusion. End sections of the archwire are often received in appliances known as buccal tubes that are fixed to the patient's molar teeth. In recent years it has become common practice to bond orthodontic appliances directly to the surface of the tooth.

For many years, it was common practice to apply orthodontic adhesive to the base of directly-bonded appliances immediately before the appliances were placed on the tooth. In some instances, a quantity of adhesive was dispensed onto a mixing pad or dispensing well and a small spatula or other hand instrument was then used to apply a small dab of adhesive to each appliance. In other instances, a quantity of adhesive was dispensed from a syringe directly onto the base of the appliance.

Adhesive precoated brackets are known and offer significant advantages to the orthodontist. Adhesive precoated brackets have a bonding base upon which the manufacturer may apply a precise quantity of adhesive such as a photo-curable adhesive. When it is desired to mount the bracket on a tooth, the bracket is simply removed from the package and placed directly onto the tooth surface.

Adhesives used on precoated brackets are, in general, more viscous (i.e., less fluid) than other available orthodontic bonding adhesives. The higher viscosity ensures that the adhesive retains its shape and does not separate or distort when the bracket is lifted from the package for use. However, some orthodontists prefer the use of less viscous (i.e., more fluid) adhesives in order to facilitate manipulation of the bracket before the adhesive is cured. For example, brackets with less viscous adhesives are relatively easy to slide along the tooth surface when an effort is made to align the bracket in a proper, precise orientation on the tooth before the adhesive is cured.

Some practitioners prefer two-part chemical-cure adhesives (such as UNITE brand adhesive, from 3M Unitek Corporation) over light-curable adhesives. Orthodontic brackets precoated with one part of a two-part adhesive on the base of the bracket have been reported. After the bracket is removed from the package, a second part is applied to the bracket base and/or the tooth surface, and the bracket is then applied to the surface of the patient's tooth. Reported packages for brackets precoated with one part of a two-part chemical-cure adhesive include, referring to FIG. 1, an assembly 10 having a carrier 12 with arms 14 and 15 to suspend the bracket 16 with adhesive 22 in the container 18, and, referring to FIG. 2, an assembly 10 with container 18 having an uneven, dimpled, or "V" shaped reservoir 19 in contact with the adhesive 22 on bracket 16. Presently, there is a need in the art for improved configurations for delivering brackets precoated with chemical-cure adhesives to the practitioner.

SUMMARY OF THE INVENTION

In one aspect, the present invention provides an article including an orthodontic bracket having a base for bonding the bracket to a tooth, a first part of an at least two-part adhesive on the base of the bracket, and a release substrate including a surface in contact with the first part. The first part of the at least two-part adhesive includes a polymerizable component, a polymerization initiator, and at least about 10% by weight, based on the total weight of the first part, of a filler including a silica filler. Preferably, the first part has a static yield stress at 28° C. of at least about 4000 dynes/cm$^2$. Preferably, the first part has a steady state viscosity of about $3 \times 10^2$ Pa-s to about $7 \times 10^4$ Pa-s at 28° C. The orthodontic bracket may optionally be provided in a kit that includes, for example, a second part of the at least two-part adhesive including a polymerizable component and an activator.

In another aspect, the present invention provides a method for bonding an orthodontic bracket to a tooth. In one embodiment, the method includes providing an orthodontic bracket having a base for bonding the bracket to a tooth, a first part of an at least two-part adhesive on the base, and a release substrate including a surface in contact with the first part, wherein the first part includes a polymerizable component, a polymerization initiator, and at least about 10% by weight, based on the total weight of the first part, of a filler including a silica filler; applying a second part of the at least two-part adhesive to the tooth surface, the second part including a polymerizable component and an activator for the polymerization initiator in the first part; separating the orthodontic bracket having the first part on the base from the release substrate; and applying the base of the bracket to the tooth surface having thereon the second part of the at least two-part adhesive. Preferably, the orthodontic bracket bonds to the tooth with an adhesion of at least about 7 Mpa.

In another aspect, the present invention provides a method for bonding an orthodontic bracket to a tooth. In one embodiment, the method includes providing an orthodontic bracket having a base for bonding the bracket to a tooth, a first part of an at least two-part adhesive on the base, and a release substrate including a surface in contact with the first part, wherein the first part includes a polymerizable component, a polymerization initiator, and at least about 10% by weight, based on the total weight of the first part, of a filler including a silica filler; separating the orthodontic bracket having the first part on the base from the release substrate; applying a second part of the at least two-part adhesive to the first part on the base of the bracket, the second part including a polymerizable component and an activator for the polymerization initiator in the first part; and applying the base of the bracket to the tooth surface. Preferably, the orthodontic bracket bonds to the tooth with an adhesion of at least about 7 MPa.

Definitions

As used herein, "orthodontic bracket" refers to any device with open or closed archwire slots intended to be bonded to the teeth including, for example, buccal tubes, lingual buttons, and cleats. Thus, the term "orthodontic bracket" does not encompass orthodontic bands. The bracket has a base for receiving adhesive and it can be made of metal, plastic, ceramic, and combinations thereof.

As used herein, a "two-part" adhesive refers to an adhesive composition having components in two separate parts, with each part being stable to hardening when stored separately. The adhesive is hardened upon contacting the two parts. As used herein, the term "adhesive" may refer to the first and/or second part of a two-part adhesive.

As used herein, "filler" means a particulate material (e.g., an inorganic oxide) in dry powder form capable of being dispersed in a resin. For example, a dental composite preferably includes a powder dispersed in a resin.

As used herein, the term "silica" refers to the compound silicon dioxide. See Kirk-Othmer Encyclopedia of Chemical Technology, 4th Ed., Vol. 21, pp. 977–1032 (1977).

As used herein, the term "amorphous silica" refers to silica that does not have a crystalline structure as defined by x-ray diffraction measurements. Examples of amorphous silica include silica sols, silica gels, precipitated silica, and pyrogenic silica.

As used herein, the terms "pyrogenic silica" and "fumed silica" are used interchangeably and refer to amorphous silicas formed in the vapor phase. Pyrogenic silica may contain, for example, a few hundred primary particles fused into branched-chain, three-dimensional aggregates. Examples of pyrogenic silica include products available under the trade designations AEROSIL OX-50, AEROSIL-130, AEROSIL-150, AEROSIL-200, and AEROSIL R-972 available from DeGussa AG, (Hanau, Germany) and CAB-O-SIL M5 and CAB-O-SIL TS720 available from Cabot Corp. (Boston, Mass.).

As used herein, "base filler" refers to fillers other than fumed silica fillers. Base fillers include, for example, non-reactive fillers (e.g., quartz fillers), reactive fillers (e.g., fluoroaluminosilicate glass), and combinations thereof.

As used herein, "silane treated" means that the surface of a particle has been modified by application of a silane (e.g., dichlorodimethylsilane). Optionally, the silane may be a coupling agent that includes a reactive functionality (e.g., γ-methacryloxypropyltrimethoxysilane, A174).

As used herein, "aggregate length" means the longest dimension of the aggregate. As used herein, "aggregate" is descriptive of strongly associated primary particles often bound together by, for example, by residual chemical treatment, covalent chemical bonds, ionic chemical bonds, or hydrogen bonds.

As used herein, "slump" refers to the phenomenon of flow under the force of gravity. It is desirable that orthodontic adhesives do not slump because after they are placed in the mouth, the practitioner wants the imparted shape to remain unchanged until the materials are cured. It is also preferable that the adhesive can support the weight of the appliance without slumping. Slumping can lead to bracket drift and skating of the adhesive coated bracket on the tooth. Materials with a sufficiently high yield stress will not slump; that is, they will not flow under the stress of gravity. The yield stress of a material is the minimum stress required to cause the material to flow, and is described in Rheology Principles, Measurements, and Applications, C. W. Macosko, VCH Publishers, Inc., New York, 1994, p. 92. If the stress due to gravity is below the yield stress of the material, then the material will not flow. The stress due to gravity will depend on the mass of the adhesive being placed and the shape. It is desirable that the yield stress of an orthodontic adhesive be sufficiently high that the material does not slump in all types and sizes of uses. Preferably, the yield stress of an orthodontic adhesive will be sufficiently high that the material does not substantially slump when supporting a bracket on top of the adhesive. If the adhesive does flow out from underneath the bracket, preferably it will remain on the release substrate when the bracket is removed.

In certain applications of orthodontic adhesives, it is desirable that the pre-cured adhesive be preapplied to an orthodontic appliance and the resulting adhesive precoated appliance packaged for later use by a practitioner. Alternatively, the adhesive can be preapplied to a release substrate and then packaged for later use by a practitioner to adhere an orthodontic appliance to a tooth. In both cases, it is critical that the packaged adhesive (whether applied on an appliance or a release substrate) does not slump over time. For certain embodiments, it is required that the preapplied (or precoated) adhesive does not slump under typical package storage and shipping conditions, for example, storage for up to 6 months, preferably for up to about 1 year, and more preferably for up to about 3 years. Generally storage would be expected to be at or below ambient temperature (i.e., room temperature), however, in some cases, storage and shipping conditions could be at greater than ambient temperature.

In order to determine or help predict the tendency of a packaged adhesive to slump over time, the adhesive can be evaluated for adhesive/bracket flow-out (or "flow-out") and/or adhesive/bracket vertical slip (or "slip") according to the test methods described herein. Briefly, flow-out measures the tendency over time of an adhesive to flow outwardly on a horizontally mounted release substrate beneath an orthodontic bracket; and slip measures the tendency of an adhesive-coated bracket vertically mounted on a release substrate to slip downward over time. For both measurements, it is preferable that the flow-out (after one week at 40° C.) and slip values are less than about 0.4 mm, more preferable less than about 0.25 mm, and most preferable 0 (zero). Flow-out or slip values greater than about 0.5 mm are readily apparent to the naked eye and can lead to significant problems during storage and/or shipping of the packaged adhesive. Such problems can include, for example, shape distortion of the adhesive on a release liner or, more seriously, separation of an orthodontic appliance from the adhesive when the appliance is removed from the package.

For such adhesive-coated, packaged articles of the present invention, it is preferable that the adhesive have a static yield stress at 28° C. of about 4000 dynes/cm$^2$ to about 100,000 dynes/cm$^2$; and have a steady state viscosity at 28° C. of about 3×10$^2$ Pascal-seconds (Pa-s) to about 7×10$^4$ Pa-s.

As used herein, the term "(meth)acrylate" is a shorthand reference to acrylate, methacrylate, or combinations thereof, and "(meth)acrylic" is a shorthand reference to acrylic, methacrylic, or combinations thereof.

As used herein, the chemical term "group" allows for substitution.

As used herein, "a" or "an" means one or more.

DETAILED DESCRIPTION OF THE PREFERRED EMBODIMENTS

Figure 1:
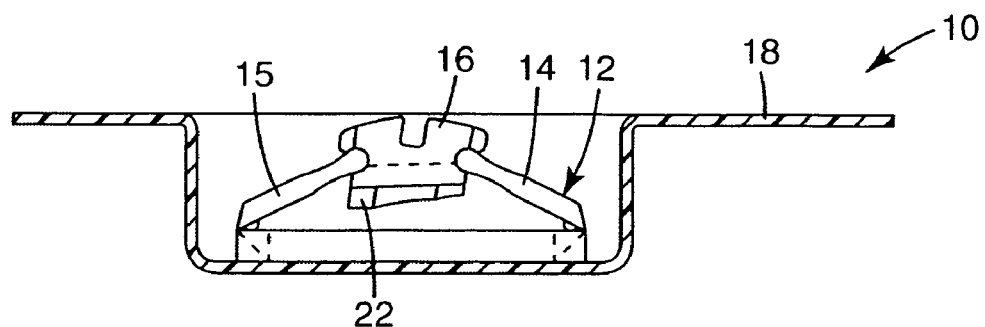
FIG. 1 is a side cross-sectional view of a prior art assembly that includes an orthodontic appliance.
Figure 2:
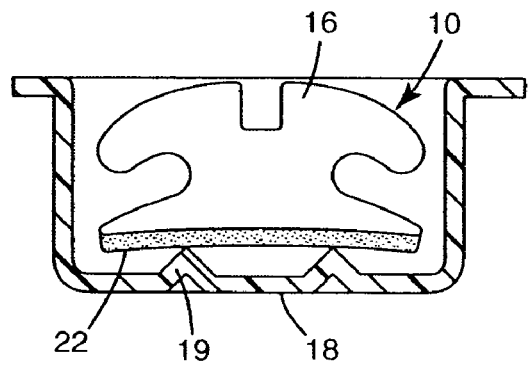
FIG. 2 is a cross-sectional view of a prior art assembly that includes an orthodontic appliance.
Figure 3:
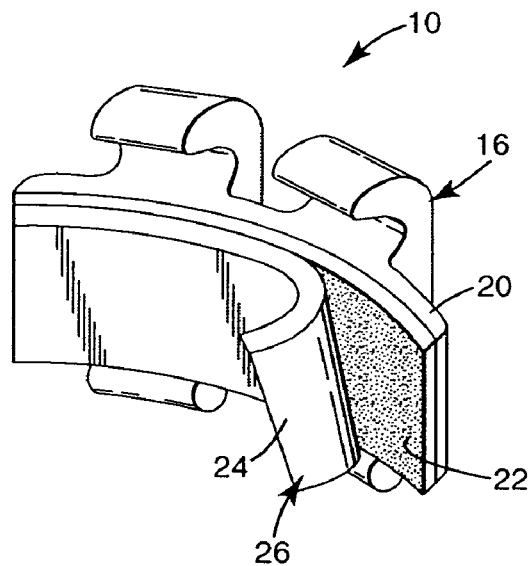
FIG. 3 is a perspective view of an orthodontic article according to one embodiment of the present invention.

Referring to FIG. 3, in one embodiment, the present invention provides article 10 including orthodontic bracket 16 having a base 20 for bonding the bracket 16 to a tooth, a first part of an at least two-part adhesive 22 on the base 20, and a release substrate 26 including a surface 24 in contact with the first part of the at least two-part adhesive 22. The release substrate 26 may be selected from a number of materials including, for example, polyolefins, poly(vinyl chloride), polyurethanes, and poly(tetrafluoroethylene). Preferably, the surface 24 of release substrate 26 comprises a number of pores, and no more than about 50% by weight of the first part 22 is within the pores. The orthodontic bracket 16 is capable of bonding to a tooth when the base 20 of the bracket 16, after being separated from the release substrate 26, is applied to a tooth surface having a second part of the at least two-part adhesive on the surface.

The first part of the at least two-part adhesive on the bracket includes a polymerizable component, a polymerization initiator, and a filler. The second part of the at least two-part adhesive preferably includes a polymerizable component and an activator.

In some embodiments, the article is preferably packaged in a container that provides barriers to the transmission of light, water vapor, and/or oxygen. In some embodiments of the present invention, the article is preferably provided as a kit. In some embodiments, the present invention preferably provides a method of bonding an orthodontic bracket to a tooth.

Some embodiments of the present invention may provide one or more additional features. For example, in some embodiments of the present invention, the first part of the at least two-part adhesive preferably has a static yield stress at 28° C. of at least about 4000 dynes/cm$^2$. In some embodiments of the present invention, the first part of the at least two-part adhesive preferably has a steady state viscosity of about $3\times10^2$ Pa-s to about $7\times10^4$ Pa-s at 28° C.

In some embodiments of the present invention, the first part of the at least two-part adhesive preferably includes at least about 10% by weight, based on the total weight of the adhesive, of a filler comprising a silica filler. Preferably, the first part further includes a base filler.

The adhesives used in the present invention are preferably substantially free of solvent, and substantially free of added water. As used herein, the term "substantially free of added water" means that the composition does not contain water that is intentionally added as a non-complexed or coordinated entity. It is understood that many materials, such as metals or glasses, contain water that is taken up from the atmosphere or is present as a coordination complex in its normal state. Water taken up by hygroscopic materials or present as a hydrate is permissibly present in the compositions described herein. Any water that is present in the composition, regardless of source, should not be present in amounts such that the water will have a deleterious effect on the long term properties of the composition. For example, water should not be present in an amount that would facilitate reaction of an acid-reactive filler with an acidic component so that lumpiness or graininess of the material develops during commercially desired storage times.

Adhesive

The adhesives used in the present invention are at least two-part adhesives. The article disclosed in the present invention includes a first part of the at least two-part adhesive on the base of an orthodontic bracket. Preferably, a second part of the at least two-part adhesive is applied to a tooth surface. When the base of the bracket is applied to the tooth surface having thereon the second part of the at least two-part adhesive, the adhesive hardens and bonds the orthodontic bracket to the tooth. Alternately, the second part may be applied to the first part on the base of the bracket, and the bracket is then applied to the tooth surface.

The first part of the at least two-part adhesive includes a polymerizable component, a polymerization initiator, and a filler. The second part of the at least two-part adhesive includes a polymerizable component and an activator. The second part of the at least two-part adhesive may optionally include a polymeric material including, for example, poly (methyl methacrylate). Exemplary two-part adhesives are disclosed, for example, in U.S. Pat. No. 5,221,202 (James). Such adhesives, however, lack high levels of silica filler, and do not provide theological properties and bond strengths desired by some practitioners for precoated adhesives.

First Part of an at Least Two-Part Adhesive

Polymerizable Component. Adhesives used in the present invention include a polymerizable component. Preferably, the polymerizable component is a monomer, oligomer, or polymer that includes a polymerizable group. Exemplary polymerizable components are disclosed, for example, in U.S. Pat. No. 6,126,922 (Rozzi et al.) and International Patent Application Publication No. WO 00/69393 (Brennan et al.). The polymerizable component may also be selected from hydrophilic and acidic components disclosed herein that are polymerizable.

Polymerizable groups may be selected from free radically polymerizable groups, cationically polymerizable groups, or combinations thereof. In a preferred aspect of the present invention, at least some of the polymerizable material is relatively lower in viscosity than other ingredients of the composition so that it serves a viscosity lowering function in the overall uncured material.

Preferred polymerizable groups are free radically polymerizable groups. Preferred free radically polymerizable components are esters of (meth)acrylic acid, including, for example, methyl (meth)acrylate, ethyl (meth)acrylate, propyl (meth)acrylate, isopropyl (meth)acrylate, 2-hydroxyethyl acrylate, 2-hydroxyethyl methacrylate ("HEMA"), hydroxypropyl (meth)acrylate, tetrahydrofurfuryl (meth)acrylate, glycidyl (meth)acrylate, the diglycidyl methacrylate of bisphenol A ("Bis-GMA"), glycerol mono(meth) acrylate, glycerol di(meth)acrylate, ethylene glycol di(meth) acrylate, poly(ethylene glycol) di(meth)acrylate (where the number of repeating ethylene oxide units vary from 2 to 30, including, for example, triethylene glycol dimethacrylate ("TEGDMA")), neopentyl glycol di(meth)acrylate, trimethylolpropane tri(meth)acrylate, mono-, di-, tri-, and tetra-(meth)acrylates of pentaerythritol and dipentaerythritol, 1,3-butanediol di(meth)acrylate, 1,4-butanediol di(meth)acrylate, 1,6-hexanediol di(meth)acrylate, di-2-methacryloyloxyethyl hexamethylene dicarbamate, di-2-methacryloyloxyethyl trimethylhexamethylene dicarbamate, di-2-methacryloyloxyethyl dimethylbenzene dicarbamate, methylene-bis-2-methacryloxyethyl-4-cyclohexyl carbamate, di-2-methacryloxyethyl-dimethylcyclohexane dicarbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxye dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2'-bis(4-methacryloxyphenyl)propane, 2,2'-bis(4-acryloxyphenyl)propane, 2,2'-bis[4-(2-hydroxy-3-methacryloxyphenyl)]propane, 2,22,2'-bis(4-methacryloxyethoxyphenyl)propane, 2,2'-bis(4-acryloxyethoxyphenyl)propane, 2,2'-bis[(4-methacryloxypropoxyphenyl)]propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis [3-(4-phenoxy)-2-hydroxypropane-1-methacrylate]propane, 2,2'-bis[3-(4-phenoxy)-2-hydroxypropane-1-acrylate]propane, and combinations thereof.

Preferably, the first part of the at least two-part adhesive includes at least about 28% by weight, more preferably at least about 30% by weight, and most preferably at least about 32% by weight polymerizable component, based on the total weight of the first part of the at least two-part adhesive. Preferably, the first part of the at least two-part adhesive includes at most about 40% by weight, more preferably at most about 38% by weight, and most preferably at most about 36% by weight polymerizable component, based on the total weight of the first part of the at least two-part adhesive.

The polymerizable component may optionally include a hydrophilic component. Preferably, a hydrophilic component is a hydrophilic monomer, oligomer, or polymer. Exemplary hydrophilic components are disclosed, for example, in U.S. Pat. No. 6,126,922 (Rozzi et al.) and International Patent Application Publication No. WO 00/69393 (Brennan et al.).

Preferred hydrophilic components include, for example, 2-hydroxyethyl acrylate, 2-hydroxyethyl methacrylate (HEMA), hydroxypropyl (meth)acrylate, glycerol di(meth)acrylate, poly(ethylene glycol) methacrylate, poly(ethylene glycol) di(meth)acrylate, poly(propylene glycol) (meth)acrylate, tetrahydrofurfuryl (meth)acrylate, glycidyl (meth)acrylate, and combinations thereof. Other preferred hydrophilic monomers include glycerol (meth)acrylate, glycerol di(meth)acrylate, ethylene glycol di(meth)acrylate, poly(ethylene glycol) di(meth)acrylate (where the number of repeating ethylene oxide units varies from 2 to 30, including, for example, tri(ethylene glycol) dimethacrylate (TEGDMA)).

Other examples of hydrophilic components include monomers and polymers such as pyrrolidone, a moiety containing hydroxy groups and polyether groups, a moiety containing a sulfonate group, a moiety containing a sulfinate group, N-oxysuccinimide, N-vinylacetamide, and acrylamide.

When hydrophilic components are present, preferably the first part of the at least two-part adhesive includes at least about 0.05% by weight, more preferably at least about 1% by weight, and most preferably at least about 3% by weight hydrophilic component, based on the total weight of the first part of the at least two-part adhesive. When hydrophilic components are present, preferably the first part of the at least two-part adhesive includes at most about 40% by weight, more preferably at most about 38% by weight, and most preferably at most about 36% by weight hydrophilic component, based on the total weight of the first part of the at least two-part adhesive.

The polymerizable component may optionally include an acidic component. Preferably, the acidic component is an acidic monomer, oligomer, or polymer. The acidic component includes at least one acidic group. The acidic group is preferably selected from oxyacids or thio-oxy acids of C and P. More preferably, the acidic component is a compound that is an acid of C or P. If desired, a precursor to the acid, such as an acid anhydride, e.g., 4-methacryloxyethyl trimellitate anhydride (4-META), or ester can be used in place of the acid itself. For example, the desired acid may be generated in situ. Preferred acids include, for example, carboxylic acids, sulfonic acids, and phenols, with carboxylic acids, alkylsulfonic acids, arylsulfonic acids, and phosphonic acids being more preferred. Exemplary hydrophilic components are disclosed, for example, in U.S. Pat. No. 6,126,922 (Rozzi et al.) and International Patent Application Publication No. WO 00/69393 (Brennan et al.).

Preferred acidic groups are carboxylic acids, sulfonic acids, phosphoric acids, phosphonic acids, and boric acids, the salts of the foregoing acids or precursors of the foregoing acids that are easily converted to these acids in conditions encountered during an orthodontic procedure. Examples of acidic components include, for example, (meth)acryloyl substituted carboxylic acids; phosphoric acid esters of hydroxyethyl (meth)acrylate, hydroxypropyl (meth)acrylate, and glycerol di(meth)acrylate; (meth)acrylates of pentaerythritol (e.g., pentaerythritol di(meth)acrylate); and (meth)acrylates of dipentaerythritol (e.g., dipentaerythritol penta(meth)acrylate), and combinations thereof.

Preferred acidic components include, for example, derivatives of amino acids, and acids such as tartaric acid, citric acid, malic acid that have been functionalized with an ethylenically unsaturated functionality. For example, citric acid may be functionalized by incorporating an acryloyl or methacryloyl functionality. A preferred example of this is CDMA, which is the reaction product of citric acid and isocyanatoethyl methacrylate.

When acidic components are present, preferably the first part of the at least two-part adhesive includes at least about 0.01% by weight, more preferably at least about 0.05% by weight, and most preferably at least about 1% by weight acidic component, based on the total weight of the first part of the at least two-part adhesive. When acidic components are present, preferably the first part of the at least two-part adhesive includes at most about 40% by weight, more preferably at most about 38% by weight, and most preferably at most about 36% by weight acidic component, based on the total weight of the first part of the at least two-part adhesive.

Polymerization initiator. The first part of the at least two-part adhesives used in the present invention includes a polymerization initiator. Preferably, the polymerization initiator is a free radical generator. Useful free radical generators include, for example, peroxides (e.g., benzoyl peroxide, dicumyl peroxide, di-t-butyl peroxide) and iodonium salts (e.g., diphenyliodonium chloride, bromide, iodide, or hexafluorophosphate). Exemplary polymerization initiators are disclosed, for example, in U.S. Pat. No. 6,126,922 (Rozzi et al.) and International Patent Application Publication No. WO 00/69393 (Brennan et al.). Preferred polymerization initiators include, for example, benzoyl peroxide.

Filler. Adhesives used in the present invention may optionally include reactive or non-reactive fillers. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler is preferably non-toxic and suitable for use in the mouth. The filler can be radiopaque, radiolucent, or non-radiopaque.

Reactive fillers include those that are commonly used with ionomers to form ionomer cements. Examples of suitable reactive fillers include metal oxides such as zinc oxide and magnesium oxide, and ion-leachable glasses including, for example, those described in U.S. Pat. Nos. 3,655,605 (Smith); U.S. Pat. No. 3,814,717 (Wilson et al.); U.S. Pat. No. 4,143,018 (Crisp et al.); U.S. Pat. No. 4,209,434 (Wilson et al.); U.S. Pat. No. 4,360,605 (Schmitt et al.), and U.S. Pat. No. 4,376,835 (Schmitt et al.). Such reactive fillers may be incorporated to modify the handling characteristics or to affect the setting properties of the ultimate composition.

The reactive filler is preferably a finely divided reactive filler. The filler should be sufficiently finely divided so that it can be conveniently mixed with the other ingredients and used in the mouth. Average particle sizes for the filler are preferably at least about 0.2 micron and more preferably at least about 1 micron. Average particle sizes for the filler are preferably at most about 15 microns and more preferably at most about 10 microns. Average particle sizes may be measured by using, for example, a sedimentation analyzer.

Preferred fillers for use in adhesives used in the present invention include acid-reactive fillers. Suitable acid-reactive fillers include metal oxides, metal salts, and glasses. Preferred metal oxides include barium oxide, calcium oxide, magnesium oxide, and zinc oxide. Preferred metal salts include salts of multivalent cations including, for example, aluminum acetate, aluminum chloride, calcium chloride, magnesium chloride, zinc chloride, aluminum nitrate, barium nitrate, calcium nitrate, magnesium nitrate, strontium nitrate, and calcium fluoroborate. Preferred glasses include borate glasses, phosphate glasses, and fluoroaluminosilicate glasses.

Most preferred of the acid reactive fillers are those that release fluoride. Fluoride releasing glasses, in addition to providing good handling and final composition properties as discussed herein, provide the benefit of long-term release of fluoride in use including, for example, use in the oral cavity. Fluoroaluminosilicate glasses are particularly preferred. Suitable acid reactive fillers are also available from a variety of commercial sources familiar to those skilled in the art. Mixtures of fillers can be used if desired.

If desired acid reactive fillers can be subjected to a surface treatment. Suitable surface treatments include acid washing, treatment with phosphates, treatment with chelating agents such as tartaric acid, and treatment with a silane or silanol coupling agent. Particularly preferred acid reactive fillers are silanol treated fluoroaluminosilicate glass fillers, as described in U.S. Pat. No. 5,332,429 (Mitra et al.).

Non-acid reactive fillers may be selected from one or more of any material suitable for incorporation in compositions used for medical applications, such as fillers currently used in dental restorative compositions and the like. Examples of suitable non-acid reactive inorganic fillers are naturally-occurring or synthetic materials such as quartz (e.g., microcrystalline silicas including, for example, those available under the trade designations IMSIL from Unimim Specialty Minerals (Elco, Ill.) and CONCISE from 3M Espe (St. Paul, Minn.)), nitrides (e.g., silicon nitride), glasses derived from, for example Ce, Sb, Sn, Zr, Sr, Ba, and Al, colloidal silica, feldspar, borosilicate glass, kaolin, talc, titania, and zinc glass; low Mohs hardness fillers such as those described in U.S. Pat. No. 4,695,251 (Randklev); and submicron silica particles (e.g., pyrogenic silicas such as the "Aerosil" Series "OX 50", "130", "150" and "200" silicas sold by Degussa and "Cab-O-Sil MS" and "Cab-O-Sil TS-720" silicas sold by Cabot Corp., Boston, Mass.). Examples of suitable non-reactive organic filler particles include filled or unfilled pulverized polycarbonates, polyepoxides, and the like. Preferred non-acid reactive filler particles include quartz, submicron silica, and non-vitreous microparticles of the type described in U.S. Pat. No. 4,503,169 (Randklev). Mixtures of non-acid reactive fillers are also contemplated, as well as combination fillers made from organic and inorganic materials.

Preferably, the surface of the filler particles is treated with a coupling agent in order to enhance the bond between the filler and the polymerizable resin. The use of suitable coupling agents include, for example, gamma-methacryloxypropyltrimethoxysilane, gamma-mercaptopropyltriethoxysilane, gamma-aminopropyltrimethoxysilane, and combinations thereof.

In some embodiments of the present invention, the adhesive preferably includes one or more silica fillers having a surface area of at least about 70 $m^2/g$, more preferably at least about 90 $m^2/g$, and most preferably at least about 100 $m^2/g$. In some embodiments of the present invention, the adhesive preferably includes one or more silica fillers having a surface area of at most about 1000 $m^2/g$, more preferably at most about 500 $m^2/g$, and most preferably at most about 150 $m^2/g$.

Preferably, the adhesive includes at least about 10% by weight, more preferably at least about 45% by weight, and most preferably at least about 50% by weight, based on the total weight of the adhesive, of a base filler. Preferably, the adhesive includes at most about 87% by weight, more preferably at most about 85% by weight, and most preferably at most about 83% by weight, based on the total weight of the adhesive, of a base filler.

Preferably, the adhesive includes at least about 0.1% by weight, more preferably at least about 0.2% by weight, and most preferably at least about 5% by weight, based on the total weight of the adhesive, of a fumed silica filler having a surface area of at least about 70 $m^2/g$. Preferably, the adhesive includes at most about 50% by weight, more preferably at most about 15% by weight, and most preferably at most about 10% by weight, based on the total weight of the adhesive, of a fumed silica filler having a surface area of at least about 70 $m^2/g$. It should be recognized that higher levels of base filler will preferably allow lower levels of fumed silica fillers to reach the desired Theological properties, and likewise lower levels of base filler will preferably allow higher levels of fumed silica fillers to reach the desired Theological properties.

Preferably, the adhesive includes a fumed silica filler having an average aggregate length of at least about 0.01 micron, more preferably at least about 0.05 micron, and most preferably at least about 0.1 micron. Preferably, the adhesive includes a fumed silica filler having an average aggregate length of at most about 1 micron, more preferably at most about 0.5 micron, and most preferably at most about 0.4 micron.

If desired, adhesives used in the present invention may optionally include adjuvants. Adjuvants include, for example, cosolvents, pigments, inhibitors, accelerators, viscosity modifiers, surfactants, rheology modifiers, colorants, medicaments, adhesion promoters and other ingredients that will be apparent to those skilled in the art. Optionally, the compositions may contain stabilizers. Suitable adjuvants include, for example, those disclosed in International Patent Application Publication No. WO 00/69393 (Brennan et al.).

Physical Properties. Adhesives used in the present invention preferably have physical properties that are desired for precoated and/or packaged orthodontic adhesives. Desirable properties include, for example, adequate handling properties, no slump that would be observable by a practitioner, no substantial flow-out, suitable operatory light stability, no observable slip when placed on liner or tooth, suitable aesthetic color, color stability under office light conditions (e.g., white light stability), and sufficient tack such that the precoated bracket does not fall off the tooth when placed there prior to curing.

The first part of the at least two-part adhesive used in the present invention preferably has a steady state viscosity at 28° C. of at least about $3 \times 10^2$ Pa-s, more preferably at least about $5 \times 10^3$ Pa-s, and most preferably at least about $1 \times 10^4$ Pa-s. The first part of the at least two-part adhesive used in the present invention preferably has a steady state viscosity at 28° C. of at most about $7 \times 10^4$ Pa-s, more preferably at most about $2.5 \times 10^4$ Pa-s, and most preferably at most about $2 \times 10^4$ Pa-s.

The first part of the at least two-part adhesives used in the present invention preferably have a static yield stress at 28° C. of at least about 4,000 dynes/cm$^2$, more preferably at least about 8,000 dynes/cm$^2$, and most preferably at least about 9,000 dynes/cm$^2$. The first part of the at least two-part adhesives used in the present invention preferably have a static yield stress at 28° C. of at most about 100,000 dynes/cm$^2$, more preferably at most about 60,000 dynes/cm$^2$, and most preferably at most about 25,000 dynes/cm$^2$.

The first part of the at least two-part adhesives used in the present invention may be applied to the base of the orthodontic appliance by methods known in the art. Suitable methods include, for example, application with a syringe or other suitable dispensing devices as disclosed, for example, in U.S. Pat. No. 5,552,177 (Jacobs et al.).

Second Part of an at Least Two-Part Adhesive

The second part of the at least two-part adhesive is also known as a primer. The second part of the at least two-part adhesive includes a polymerizable component, as described herein, and an activator. The second part of the at least two-part adhesive may optionally include a polymeric material including, for example, poly(methyl methacrylate) and/or a coupling agent (e.g., γ-methacryloxypropyltrimethoxysilane available under the trade designation A174 from Witco Osi Specialties (Danbury, Conn.)).

The second part of the at least two-part adhesives used in the present invention includes an activator. Preferably, the activator interacts with the polymerization initiator to cause the production of free radicals. Useful activators for free radical polymerization initiators include, for example, electron donors (e.g., sodium benzene sulfinate, amines, and amino alcohols). Exemplary activators are disclosed, for example, in U.S. Pat. No. 6,126,922 (Rozzi et al.) and International Patent Application Publication No. WO 00/69393 (Brennan et al.). Preferred activators are electron donors, and amines are more preferred. Preferred amine electron donors include, for example, N,N-bis-(2-hydroxyethyl)-p-toluidine.

Preferably, the second part of the at least two-part adhesive includes at least about 3% by weight, more preferably at least about 5% by weight, and most preferably at least about 7% by weight activator, based on the total weight of the second part of the at least two-part adhesive. Preferably, the second part of the at least two-part adhesive includes at most about 30% by weight, more preferably at most about 25% by weight, and most preferably at most about 20% by weight activator, based on the total weight of the second part of the at least two-part adhesive.

Preferably, the second part of the at least two-part adhesive includes at least about 80% by weight, more preferably at least about 82% by weight, and most preferably at least about 85% by weight polymerizable component, based on the total weight of the second part of the at least two-part adhesive. Preferably, the second part of the at least two-part adhesive includes at most about 95% by weight, more preferably at most about 93% by weight, and most preferably at most about 90% by weight polymerizable component, based on the total weight of the second part of the at least two-part adhesive.

Preferably, the second part of the at least two-part adhesive includes at least about 1% by weight, more preferably at least about 1.5% by weight, and most preferably at least about 2% by weight polymeric material, based on the total weight of the second part of the at least two-part adhesive. Preferably, the second part of the at least two-part adhesive includes at most about 10% by weight, more preferably at most about 7% by weight, and most preferably at most about 5% by weight polymeric material, based on the total weight of the second part of the at least two-part adhesive.

Preferably, the second part of the at least two-part adhesive includes at least about 0.1% by weight, more preferably at least about 0.25% by weight, and most preferably at least about 0.5% by weight of a coupling agent, based on the total weight of the second part of the at least two-part adhesive. Preferably, the second part of the at least two-part adhesive includes at most about 2% by weight, more preferably at most about 1.5% by weight, and most preferably at most about 1.25% by weight of a coupling agent, based on the total weight of the second part of the at least two-part adhesive.

The second part of the at least two-part adhesive used in the present invention preferably has a steady state viscosity at 28° C. of at least about 0.1 Pa-s, more preferably at least about 0.15 Pa-s, and most preferably at least about 0.175 Pa-s. The second part of the at least two-part adhesive used in the present invention preferably has a steady state viscosity at 28° C. of at most about 0.4 Pa-s, more preferably at most about 0.35 Pa-s, and most preferably at most about 0.3 Pa-s.

Release Substrate

Articles of the present invention preferably include a release substrate in contact with the adhesive. Preferably, a surface of the release substrate includes a number or pores, and no more than about 50% by weight of the adhesive is in the pores. Preferably, the release substrate includes a foam. Suitable release substrates are disclosed, for example in U.S. Pat. No. 6,183,249 (Brennan et al.). Preferably, the release substrate is a crosslinked polyethylene foam available under the trade designation MINICEL (e.g., MINICEL M200) from Voltek (Lawrence, Mass.). Preferably, the release substrate provides for easy release of the appliance and reduced slip and flow-out.

The release substrates used in the present invention may be applied to the adhesive on the base of the orthodontic appliance by methods known in the art. Suitable methods include, for example, placing the release substrate on the bottom of a container well and then lightly inserting the bracket in the well such that the adhesive is in contact with the release substrate. A robotic arm may be used, for example, as described in U.S. Pat. No. 5,552,177 (Jacobs et al.).

The articles of the present invention are preferably packaged in a container for storage and distribution. Suitable containers include, for example, those disclosed, for example, in U.S. Pat. Nos. 4,978,007 (Jacobs et al.), U.S. Pat. No. 5,172,809 (Jacobs et al.), U.S. Pat. No. 5,328,363 (Chester et al.), U.S. Pat. No. 5,354,199 (Jacobs et al.), U.S. Pat. No. 5,538,129 (Chester et al.), U.S. Pat. No. 5,575,645 (Jacobs et al.), and in coassigned U.S. patent application Ser. No. 10/126.804 (published as U.S. 2003-01 96914 A1), filed on 8 Apr. 2002, and entitled "CONTAINERS FOR PHOTOCURABLE MATERIALS" Optionally, the container may include a release substrate. The release substrate may optionally be part of the container, but preferably the release substrate is a release liner.

The articles disclosed in the present invention may be included in kits. In addition to having one or more articles of the present invention, kits preferably include additional components including, for example, instructions for using the orthodontic appliance, a second part of the at least two-part adhesive, etching compositions, swabs or brush tips for etching compositions, appliance placement guides or jigs, extra quantities of adhesive, primer, sealant, and mix pads.

Methods of using the presently disclosed article include separating the orthodontic bracket from the release substrate, wherein the first part of the at least two-part adhesive preferably remains on the base of the orthodontic bracket. Preferably, the second-part of the at least two-part adhesive is applied to the surface of the tooth by the practitioner, although the second part of the at least two-part adhesive may also be applied to the first part on the orthodontic bracket by the practitioner. The orthodontic bracket is then applied to the tooth surface and positioned properly by the practitioner so that the adhesive is in intimate contact with the surface of the tooth. When properly positioned and the two parts of the adhesive are in intimate contact, the adhesive hardens and bonds the orthodontic bracket to the tooth. Optionally, the surface of the tooth may be etched and dried before adhering the adhesive-coated bracket to the tooth.

Preferably, when about 1 g of the first part of the two-part adhesive is mixed with about 0.3 g of the second part of the two-part adhesive, the adhesive sets at about 15 seconds to about 50 seconds at room temperature. Setting can be determined by probing the adhesive mix with a sharp probe. The adhesive is set when hand pressure with the probe does not cause the adhesive to yield.

Preferably, after the two parts are applied and hardened, the bracket is bonded to the tooth with a bond strength of at least about 7 MPa, more preferably at least about 9 MPa, and most preferably at least about 11 MPa. Preferably, after the adhesive is hardened, the bracket is bonded to the tooth with a bond strength of at most about 25 MPa.

The present invention is illustrated by the following examples. It is to be understood that the particular examples, materials, amounts, and procedures are to be interpreted broadly in accordance with the scope and spirit of the invention as set forth herein.

EXAMPLES

The following examples are given to illustrate, but not limit, the scope of this invention. Unless otherwise indicated, all parts and percentages are by weight and all molecular weights are weight average molecular weight. Unless otherwise specified, all chemicals used are commercially available from, for example, Sigma-Aldrich (St. Louis, Mo.).

| ABBREVIATIONS, DESCRIPTIONS, AND SOURCES OF MATERIALS | |
|---|---|
| BisGMA | 2,2-Bis[4-(2-hydroxy-3-methacryloyloxypropoxy)-phenyl]propane (CAS No. 1565-94-2) |
| TegDMA | triethylene glycol dimethacrylate (CAS No. 109-16-0) |
| BisEMA | two-mole ethoxylated bisphenol A dimethacrylate available under the trade designation SR 348 from Sartomer (Exton, PA) |
| DHEPT | N,N-bis-(2-hydroxyethyl)-p-toluidine (CAS No. 3077-12-1) |
| BHT | 2,6-Di-tert-butyl-4-methylphenol (Sigma-Aldrich) |
| BPO | Benzoyl peroxide (CAS No. 94-36-0) |
| TS720 | Fumed (pyrogenic) silica; surface-treated with dimethyl silicone fluid; surface area about 105 to about 130 $m^2$/gram (CAB-O-SIL TS270, Cabot Corp. Boston, MA) |
| R-972 | Fumed (pyrogenic) silica; surface-treated with dimethyldichlorosilane; surface area about 90 to about 130 $m^2$/gram (AEROSIL R-972, Degussa Corp., Akron, OH) |
| R-974 | Fumed (pyrogenoc) silica; surface-treated with dimethyldichlorosilane; surface area about 150 to about 190 $m^2$/gram (AEROSIL R-974, Degussa Corp., Akron, OH) |
| IMSIL A10 | A quartz (microcrystalline silica) filler, Unimim Specialty Minerals (Elco, Ill) |
| CONCISE | A silanted mixture of 98.5% quartz and 1.5% Aerosil R972. Filler has a surface area of about 2.20 to about 2.97 $m^2$/g, and a particle size distribution of <40 micons (87.56%), <10 microns (43.57%), and <1 micron (5.19%), 3M Espe (St. Paul, MN) |
| A174 | γ-methacryloxypropyltrimethyoxysilane, Witco Osi Specialties (Danbury, CT) |
| PMMA | Poly(methyl methacrylate), benzoyl peroxide free (CAS No. 9011-14-7) |

Test Methods

Static Yield Stress and Steady State Viscosity

Measurement of the yield stress and viscosity of adhesive test samples was performed with a Rheometrics ARES controlled strain rheometer (Advanced Rheometric Expansion System, Rheometric Scientific, Inc., Piscataway, N.J.). The rheometer was fitted with parallel plates of 25-mm diameter. An environmental chamber held the temperature in the immediate vicinity of the fixtures and sample at 28° C. Adhesive samples were prepared at least 24 hours prior to measurement by pressing the samples between two sheets of SCOTCHPAK 1022 release liner (3M Company) to a thickness of approximately 2.5 mm and a diameter of at least 25 mm.

These samples were placed on the lower plate of the rheometer using a spatula to facilitate removal from the release liner. The upper plate was lowered until contact with the adhesive sample was made. The environmental chamber was then closed and the rheometer set to automatically close the plates to a gap of 2.2 mm. The chamber was then opened and the excess adhesive trimmed from the edges of the plates using a razor blade. The chamber was then closed again and the rheometer set to automatically close the plates to a gap of 2.0 mm.

After closing the chamber the rheometer was then programmed to wait for 10 minutes for the temperature to stabilize at 28° C. before beginning the measurement. The rheometer was then programmed to shear the adhesive sample at a shear rate of 0.01 $second^{-1}$ for 30 seconds followed by shearing at 0.1 second$^{-1}$ for 4.5 minutes. During each of these periods the rheometer collected stress measurements.

The yield stress of an adhesive sample was defined as the point at which the stress vs. time curve deviated from an initially linear trajectory. Practically, this was determined by constructing a tangent to the stress vs. time curve. The tangent was then shifted by 0.06 seconds to the right and the intercept with the stress vs. time curve determined. This intercept, being very close to the point of deviation from linearity, was defined as the static yield stress (or as the transition from elastic deformation to viscoelastic flow) and reported as dynes/cm$^2$ for the adhesive sample. Reported values were from single measurements of the samples.

The adhesive samples were thixotropic, meaning that the viscosity under constant shear rate changes with time. Therefore, the viscosity of an adhesive sample was defined as the viscosity measured after a given time under shear. This time was chosen such that any yield stresses would have been overcome. A period of 3.5 minutes at 28° C. under a shear rate of 0.1 second$^{-1}$) was chosen since by that time all of the adhesive samples measured were well beyond yielding. The results were reported as steady state viscosity values (from single measurements) in units of Pa-s (Pascal-seconds).

Adhesive/Bracket Flow-Out

The Adhesive/Bracket Flow-Out Test Method was used to determine the tendency of an adhesive to flow on a liner beneath an orthodontic bracket, a phenomenon called "flow-out". If an adhesive exhibits flow-out on a specific liner in this test, then the adhesive would be expected to flow-out within a blister package containing the adhesive precoated on a bracket and covered with the same liner. Flow-out can produce stringing of the adhesive away from the bracket base as the adhesive precoated bracket is removed from the liner. This result can cause difficulties for a practitioner who must then make adjustments to the shape of the adhesive pad (or pillow) prior to placement of the adhesive precoated bracket on the tooth. In the worst case, flow-out prevents full release of the adhesive from the liner, which may even cause separation of the adhesive from the precoated bracket.

Mini Twin V-slot brackets (3M Unitek, Ref # 017-333 or 017-334) were coated by application from a syringe with about 8 mg of adhesive placed on a SCOTCHPAK 1022 release liner (3M Company) with the adhesive in contact with the liner, and held for one week in a 40° C. oven. (Time and temperature of the test was varied depending upon the test sample.) The adhesive precoated brackets were placed on liners that were held to cardboard via double stick tape in order to keep the brackets in a horizontal position in the oven. Special precaution was taken to ensure that no adhesive was visible beyond the bracket base at the start of the test. After 1 week (or other pre-determined time), adhesive flow-out beyond the bracket base was measured using RAM Optical Instrumentation (Omis Mini with AutoMap XYZ measurement software, RAM Optical Instrumentation, Huntington Beach, Calif.). Flow-out values were measured only for the worst edge (i.e., greatest flow-out) of each bracket base (rather than taking an average of flow-out on each of the 4 edges of the bracket base) and each reported value was an average of at least 3 adhesive precoated bracket samples. It is noted that about 0.01 inch (about 0.25 mm) of flow-out is barely detectable to the naked eye; however, 0.02 inch (about 0.51 mm) is readily detectable to the naked eye and can lead to problems of adhesive separation from the release liner.

Adhesive/Bracket Vertical Slip

The Adhesive/Bracket Vertical Slip Test Method was developed to determine if adhesive precoated brackets using specific adhesive compositions would slip on specific release liners in blister packages. If an adhesive exhibits slippage on a specific liner in this test, then the adhesive would be expected to slip (e.g., during transit to the customer) within a blister package containing the adhesive precoated on a bracket and covered with the same liner. In the worst case, the adhesive precoated brackets may slip entirely off the liner, destroying the product functionality. Or, the adhesive precoated bracket may rotate in the package, which would result in improper orientation for placement of the bracket on the tooth by the practitioner.

3M Unitek Mini Twin V-slot, (Ref. 017-333 or 017-334) or buccal tubes (Ref. 067-8033) or Victory Series (Ref. 017-401) brackets were coated by application from a syringe with about 8 mg of adhesive (with the exception of buccal tubes which were coated with about 16 mg of adhesive). The adhesive precoated brackets were placed on MINICEL M200 foam liner (Voltek Corp, Division of Sekisui America, Lawrence, Mass.). Each liner containing the adhesive precoated bracket was held to a piece of cardboard via double stick tape. Special precaution was taken to ensure that no adhesive was visible beyond the bracket base at the start of the test. A "starting line" was drawn near the top edge of the bracket to ensure measurement of the exact distance of slippage. The cardboard containing the brackets was held vertically in an oven (set at a predetermined temperature, typically 40° C. or 50° C.) for predetermined period of time (typically 3 to 14 days). Slippage of the adhesive coated bracket on the liner was measured as flow-out beyond the top edge of the bracket base and was measured using RAM Optical Instrumentation as described in the preceding test method. The slippage values reported (in mm) were an average of at least 3 adhesive precoated bracket samples per test.

Materials Preparation

Silanation of Quartz Filler

An amount of distilled water equal to the amount of IMSIL A-10 (Unimin Specialty Minerals, Inc. Elco, Ill.) to be silanated was placed into a HDPE drum. The pH was adjusted to 3.0 to 3.5 using glacial acetic acid. This solution was stirred continuously using a non metallic mixer. Silane A-174 was added to the water while stirring at high speed. The amount of silane was 5.25% of the IMSIL to be treated. Mixing was continued for 45 to 50 minutes. IMSIL was slowly added into the vortex of the mixer. After all the IMSIL was added stirring was continued for 2 to 2.5 hours. The mixer was removed, the container was covered, and the IMSIL was allowed to settle. After the IMSIL had settled, the liquid was decanted off. The wet IMSIL was placed into shallow glass dishes and placed in a 40° C. oven for several days until dry. The temperature was raised to 120° C. and the dried material was heated for 16 to 24 hours. The material was allowed to cool to room temperature. The dry material was sifted through a fine mesh nylon screen.

Example 1

The first part of a two-part adhesive was made by combining the following ingredients:

TABLE 1

First Part Formulations (Percent by Weight)

| | Example 1 (First Part) |
|---|---|
| TegDMA | 14.65 |
| BisGMA | 18.10 |
| BPO | 0.98 |
| BHT | 0.069 |
| Silanated IMSIL | 57.2 |
| Aerosil R972 | 8.00 |
| Cab-O-Sil TS-270 | 1.00 |

The first part was prepared according to the following general procedure. A premeasured amount of BisGMA was removed from the refrigerator and allowed to warm to room temperature. TegDMA was weighed into a separate container. The BisGMA and TegDMA containers were placed into an oven preheated to about 45° C. to about 55° C. for about 2–3 hours. The TegDMA was then poured into the BisGMA with manual stirring. After a uniform solution was obtained, the material was cooled to less than about 30° C. Weighed amounts of BPO and BHT were added to the material and the material was stirred for at least 4 hours until a uniform solution was obtained.

The material was then transferred to a tared Hobart mixing bowl. Aerosil R972 was weighed into the bowl and a weighed amount of silanated IMSIL was sprinkled onto the Aerosil and resin mixture. The material was mixed at low or medium speed for at least 75 minutes while scraping the material from the sides of the bowl, until a uniform mixture was obtained. Mixing was started immediately after addition of the IMSIL and Aerosil to the mixer. A minimum amount of Cab-O-Sil TS720 was then added to the mixing bowl, and it was stirred at the lowest speed until a uniform mixture is obtained. Additional Cab-O-Sil may be added to provide a material with increased viscosity.

The second part of the two-part adhesive was made by combining the following ingredients:

TABLE 2

Second Part Formulations (Percent by Weight)

| | Example 1 (Second Part) |
|---|---|
| BisGMA | 9.5 |
| TegDMA | 76.9 |
| DHEPT | 10.0 |
| A174 | 1.12 |
| PMMA | 2.5 |

The second part was prepared according to the following general procedure. A premeasured amount of BisGMA was placed in a container sufficient to hold the completed batch was removed from regrigerated storage and allowed to warm to room temperature. TegDMA was measured into a separate container. Both containers were placed in an oven preheated to 45° C. to about 55° C. for about 2–3 hours. The TegDMA was then poured into the BisGMA with manual stirring. Mechanical stirring was then started, and the container was heated on a hot plate until the temperature was about 50° C. to 55° C.

After the temperature reached 50° C. and all the BisGMA had dissolved, measured amounts of DHEPT and A174 were added. When they had completely dissolved, an amount of PMMA equal to 2.5% of the total formulation was added to the container. This mixture was stirred for at least two hours while the temperature was maintained at 50° C. to 55° C. The container was then placed in an oven preheated to about 45° C. to about 55° C. and allowed to set for about 15 to about 20 hours until clear. The mixture was then cooled to room temperature.

Comparative Example 1

The first part of a comparative two-part adhesive was made by combining the following ingredients:

TABLE 3

Comparative First Part Formulations (Percent by Weight)

| | Comparative Example 1 (First Part) |
|---|---|
| BisEMA | 34.81 |
| BisGMA | 54.27 |
| BPO | 2.97 |
| BHT | 1.00 |
| Aerosil R974 | 6.93 |

The comparative first part was prepared according to the following general procedure. BisEMA (7.03 g) was placed in a mixing cup. BHT (0.203 g) was weighed into the cup. The cup was then placed in a centrifugal mixer (SPEED MIXER DAC 150 FVZ, FlackTek, Inc.) and spun at 3000 revolutions per minute (rpm) for 2 minutes. The BHT was not fully dissolved, so the cup was spun for another 2 minutes at 3000 rpm. The BHT was still not fully dissolved, so the cup was placed in an oven at 50° C. for 10 minutes. After spinning for 2 minutes at 3000 rpm, the BHT was dissolved.

BPO (0.6008 g) was weighed into the cup. Spinning at 3000 rpm for 2 minutes dispersed the powder throughout the resin. The paste was then warmed at 40° C. and stirred with a magnetic stir bar overnight to dissolve the BPO. BisGMA (10.96 g) was weighed into the cup. The cup was placed in an oven at 50° C. for 30 minutes then mixed with a magnetic stir bar on a hot plate. Aerosil R974 (1.3995 g) was added to the cup, followed by spinning at 3000 rpm for 2 minutes. Visual inspection revealed the paste to be very uniform.

The comparative second part of the two-part adhesive was made by combining the following ingredients:

TABLE 4

Comparative Second Part Formulations (Percent by Weight)

| | Comparative Example 1 (Second Part) |
|---|---|
| BisGMA | 63.70 |
| TegDMA | 27.22 |
| DHEPT | 2.72 |
| Aerosil R974 | 6.35 |

The comparative second part was prepared according to the following general procedure. TegDMA (6.00 g) was weighed into a mixing cup. DHEPT (0.6005 g) was added to the cup. The mixture was then warmed at 40° C. and stirred with a magnetic stir bar overnight to dissolve the DHEPT. BisGMA (14.04 g) was added to the cup. The cup was then placed in an oven at 50° C. for 30 minutes. Aerosil R974 (1.400 g) was added to the cup. Spinning at 3000 rpm for 2 minutes yielded a uniform mixture.

Example 2

Bond Strength

The two-part adhesives were employed to bond brackets to bovine teeth using the following procedure. Bovine teeth were mounted in acrylic denture base material so that the labial surfaces were exposed. The mounted teeth were cleaned with a slurry of pumice in water. The teeth were then etched with Transbond XT etching gel (3M Unitek) for 15 seconds apiece before rinsing with water. The teeth were then dried with oil-free compressed air and examined to ensure the presence of a chalky white texture that indicates a sufficient etch. The first part of the two-part adhesive was applied via syringe to the bonding base of VICTORY SERIES REF 017-401 (or equivalent) upper central brackets (3M Unitek). The second part of the two-part adhesive was painted onto the surface of each tooth. Each bracket was pressed in place on a tooth. Excess flash was cleaned from the periphery of the bonding base. The bonded brackets were allowed to sit at room temperature for a period of 10 minutes before submerging them in 37° C. water for 24 hours. The bonded brackets were removed from the water and mounted with the gingival tie wings pointing vertically in a test fixture attached to an Instron 4204 testing machine. A 0.020 inch diameter standard round wire was looped under the occlusal tie wings and attached to the crosshead of the testing machine. After moving the crosshead to make the wire snug, it was set to move at 5 mm/minute until the bracket was debonded. The maximum force (in units of pounds) was recorded as bond strength per bracket and the reported value was an average of 10 measurements using 10 different adhesive-coated brackets. This average was then converted to units of MPa by dividing by the bonding base area (10.9 $mm^2$) and multiplying by 4.4.

Using the Example 1 first and second parts resulted in a bond strength of 15.5 MPa. Using the Comparative Example 1 first and second parts resulted in a bond strength of 2.8 MPa. As can be seen from the bond strength data, Comparative Example 1 produced much lower bond strength. Qualitative inspection of the teeth post-debonding revealed that the Comparative Example 1 paste was still soft underneath the bracket, indicating that it was not fully-cured. During bonding, the first and second parts of the Comparative Example 1 two-part adhesive were found to be very gooey and difficult to work with. Upon cleaning the excess from the periphery of the bonding base, some of the paste tended to get stuck on the tie wings.

Example 3

Bond Strength for Bicuspid Brackets

Biscupid brackets (e.g., having a curved base) were bonded to bovine teeth to determine the bond strength for thicker cross-section adhesives using the following procedure. Bovine teeth (20) were pumiced, rinsed, and dried. The teeth were then etched with 37% phosphoric acid for 15 seconds, rinsed, and dried. All the teeth were primed with a light coat of the Example 1, second part of the two-part adhesive. Ten brackets were primed with a light coat of the Example 1, second part of the two-part adhesive, and ten brackets were not primed. A small amount of the Example 1, first part of the two-part adhesive was applied to each bracket. The brackets were placed on the bovine teeth, the flash was cleaned, and after 5 minutes, the teeth were placed in 37° C. water for 24 hours. The bond strength was tested as described in Example 2.

The unprimed brackets resulted in a bond strength of 17 MPa. The primed brackets resulted in a bond strength of 20 MPa. The bond strengths for the unprimed brackets suggest that the first part of the two-part adhesive is suitable for use as on precoated brackets.

Example 4

Packaging

Some of the requirements of the packaging for a precoated adhesive are that the adhesive support the appliance, the adhesive remain on the bonding base upon removal from the package, and that the package ensures that the adhesive is still functional after some years in storage.

The performance of the Example 1 and Comparative Example 1 two-part adhesives in supporting a buccal tube were tested. When placed on a sheet of polyvinyl chloride (PVC), the Comparative Example 1 paste flowed out readily from underneath buccal tubes, while the Example 1 paste did not.

Additionally, when removing a bracket coated with the Comparative Example 1 paste from the PVC substrate, much of the adhesive was left behind, while the Example 1 paste was removed cleanly from a foam substrate.

Twenty VICTORY SERIES 068-8522 buccal tubes were coated by hand with Example 1 first part samples and placed on a sample of Minicell M200 foam liner. Some of the samples were placed vertically on a laboratory bench for 1 week at room temperature. Minimal sliding of the brackets and adhesive on the foam liner material was observed. Additional samples were placed horizontally on a laboratory bench for 1 week at room temperature. Minimal flow of the adhesive from under the brackets was observed. All the above buccal tubes were removed from the foam using cotton pliers. In all cases, the adhesive remained on the bracket, indicating that the adhesive satisfactorily releases from the foam liner.

Precoated Example 1 first part samples were stored at elevated temperature (40° C.) for up to sixteen weeks with little or no effect on bonding effectiveness. After this treatment, the paste still gave a bond strength of 12.6 MPa.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An article comprising:
   an orthodontic bracket having a base for bonding the bracket to a tooth;
   a first part of an at least two-part adhesive on the base of the bracket, the first part comprising a polymerizable component, a polymerization initiator, and at least about 10% by weight, based on the total weight of the first part, of a filler comprising a silica filler, with the proviso that the first part is not a light-curable adhesive; and a release substrate comprising a surface in contact with the first part.

2. The article of claim 1 wherein the first part has a static yield stress at 28° C. of at least about 4000 dynes/cm$^2$.

3. The article of claim 1 wherein the first part has a steady state viscosity of about $3 \times 10^2$ Pa-s to about $7 \times 10^4$ Pa-s at 28° C.

4. The article of claim 1 wherein the surface of the release substrate comprises a number of pores, and no more than about 50% by weight of the first part is within the pores.

5. The article of claim 1 wherein the release substrate comprises a foam.

6. The article of claim 1 packaged in a container that provides a barrier to the transmission of water vapor.

7. The article of claim 1 wherein the silica filler comprises a quartz filler.

8. The article of claim 7 wherein the quartz filler comprises a silane treated surface.

9. The article of claim 1 wherein the first part further comprises a base filler.

10. The article of claim 9 wherein the base filler is selected from the group consisting of quartz filler, fluoroaluminosilicate glass filler, and combinations thereof.

11. The article of claim 1 wherein the silica filler comprises a fumed silica.

12. The article of claim 11 wherein the fumed silica has a surface area of at least about 70 m$^2$/g.

13. The article of claim 12 wherein the fumed silica has a surface area of about 70 m$^2$/g to about 1000 m$^2$/g.

14. The article of claim 13 wherein the fumed silica has a surface area of about 90 m$^2$/g to about 500 $^2$/g.

15. The article of claim 14 wherein the fumed silica has a surface area of about 100 m$^2$/g to about 150 m$^2$/g.

16. The article of claim 11 wherein the fumed silica comprises a silane treated surface.

17. The article of claim 11 wherein the fumed silica comprises a silicone fluid treated fumed silica.

18. The article of claim 11 wherein the silicone treated fumed silica comprises a poly(dimethylsiloxane) fluid treated fumed silica.

19. The article of claim 11 wherein the first part further comprises a base filler.

20. The article of claim 19 wherein the base filler is present at about 10% by weight to about 87% by weight, based on the total weight of the first part, and the fumed silica filler is present at about 0.1% by weight to about 50% by weight, based on the total weight of the first part.

21. The article of claim 19 wherein the base filler is present at about 45% by weight to about 85% by weight, based on the total weight of the first part, and the fumed silica filler is present at about 0.2% by weight to about 15% by weight, based on the total weight of the first part.

22. The article of claim 11 wherein the fumed silica has an average aggregate length of about 0.01 micron to about 1 micron.

23. The article of claim 1 wherein the silica filler comprises a quartz filler, a fumed silica with a silane treated surface, and a silicone fluid treated fumed silica.

24. The article of claim 1 wherein the polymerizable component is selected from the group consisting of triethyleneglycol dimethacrylate, the diglycidyl methacrylate of bisphenol A, and combinations thereof.

25. The article of claim 1 wherein the orthodontic bracket bonds to a tooth with an adhesion at least about 7 MPa when the base of the bracket, after being separated from the release substrate, is applied to a tooth surface having thereon a second part of the at least two-part adhesive, the second part comprising a polymerizable component and an activator.

26. The article of claim 1 wherein the orthodontic bracket bonds to a tooth with an adhesion of at least about 7 Mpa when the base of the bracket, after being separated from the release substrate and having a second part of the at least two-part adhesive applied thereto, is applied to a tooth surface, and wherein the second part comprises a polymerizable component and an activator.

27. A kit comprising:
an orthodontic bracket having a base for bonding the bracket to a tooth, a first part of an at least two-part adhesive on the base, and a release substrate comprising a surface in contact with the first part, wherein the first part comprises a polymerizable component, a polymerization initiator, and at least about 10% by weight, based on the total weight of the first part, of a filler comprising a silica filler; and a second part of the at least two-part adhesive comprising a polymerizable component and an activator.

28. The kit of claim 27 wherein the surface of the release substrate comprises a number of pores, and no more than about 50% by weight of the first part is within the pores.

29. The kit of claim 27 further comprising an etching composition.

30. The kit of claim 27 wherein the orthodontic bracket bonds to a tooth with an adhesion of at least about 7 MPa when the base of the bracket, after being separated from the release substrate, is applied to a tooth surface having thereon the second part of the at least two-part adhesive.

31. The kit of claim 27 wherein the orthodontic bracket bonds to a tooth with an adhesion of at least about 7 MPa when the base of the bracket, after being separated from the release substrate and having the second part of the at least two-part adhesive applied thereto, is applied to a tooth surface.

32. A method for bonding an orthodontic bracket to a tooth comprising:
providing an orthodontic bracket having a base for bonding the bracket to a tooth, a first part of an at least two-part adhesive on the base, and a release substrate comprising a surface in contact with the first part, wherein the first part comprises a polymerizable component, a polymerization initiator, and at least about 10% by weight, based on the total weight of the first part, of a filler comprising a silica filler;

applying a second part of the at least two-part adhesive to the tooth surface, the second part comprising a polymerizable component and an activator for the polymerization initiator in the first part;

separating the orthodontic bracket having the first part on the base from the release substrate; and applying the base of the bracket to the tooth surface having thereon the second part of the at least two-part adhesive.

33. The method of claim 32 further comprising applying an etching composition to the tooth surface.

34. The method of claim 32 wherein the orthodontic bracket bonds to the tooth with an adhesion of at least about 7 MPa.

35. A method for bonding an orthodontic bracket to a tooth comprising:
providing an orthodontic bracket having a base for bonding the bracket to a tooth, a first part of an at least two-part adhesive on the base, and a release substrate comprising a surface in contact with the first part, wherein the first part comprises a polymerizable component, a polymerization initiator, and at least about 10% by weight, based on the total weight of the first part, of a filler comprising a silica filler;

separating the orthodontic bracket having the first part on the base from the release substrate;

applying a second part of the at least two-part adhesive to the first part on the base of the bracket, the second part comprising a polymerizable component and an activator for the polymerization initiator in the first part; and applying the base of the bracket to the tooth surface.

36. The method of claim 35 further comprising applying an etching composition to the tooth surface.

37. The method of claim 35 wherein the orthodontic bracket bonds to the tooth with an adhesion of at least about 7 MPa.

* * * * *

UNITED STATES PATENT AND TRADEMARK OFFICE
CERTIFICATE OF CORRECTION

PATENT NO. : 7,217,124 B2
APPLICATION NO. : 10/126019
DATED : May 15, 2007
INVENTOR(S) : David K. Cinader, Jr.

It is certified that error appears in the above-identified patent and that said Letters Patent is hereby corrected as shown below:

Column 6
Line 10, Delete "theological" and insert -- rheological --, therefor.
Line 59-60, Delete "methacryloxye" and insert -- methacryloxyethyl-hexamethylene --, therefor.

Column 7
Line 13, After "propane," delete "2,22,2'" and insert -- 2,2'-bis[4-(hydroxy-3-acryloxyphenyl)propane, 2,2' --, therefor.
Line 15, Delete "bis[" and insert -- bis --, therefor.
Line 16, Delete "]propane," and insert -- propane, --, therefor.

Column 10
Line 6, Delete ""Cab-O-Sil MS"" and insert -- "Cab-O-Sil M5" --, therefor.
Line 51, Delete "Theological" and insert -- rheological --, therefor.
Line 54, Delete "Theological" and insert -- rheological --, therefor.

Column 13
Line 7, Delete "Nos." and insert -- No. --, therefor.
Line 12, Delete "10/126.804" and insert -- 10/126,804 --, therefor.
Line 12, Delete "2003-01 96914 A1" and insert -- 2003-0196914 A1 --, therefor.
Line 14, After "MATERIALS"" insert -- . --.

Column 14
Line 22, Delete "pyrogenoc" and insert -- pyrogenic --, therefor.
Line 26, Delete "silanted" and insert -- silanated --, therefor.
Line 28, Delete "micons" and insert -- microns --, therefor.
Line 30, Delete "γ-methacryloxypropyltrimethyoxysilane" and insert -- γ-methacryloxypropyltrimethoxysilane --, therefor.

Column 15
Line 22, After "second$^{-1}$" delete ")".

Column 17
Line 17, Delete "TS-270" and insert -- TS-720 --, therefor.

Column 19
Line 59, Delete "Biscupid" and insert -- Bicuspid --, therefor.

UNITED STATES PATENT AND TRADEMARK OFFICE
CERTIFICATE OF CORRECTION

| | |
|---|---|
| PATENT NO. | : 7,217,124 B2 |
| APPLICATION NO. | : 10/126019 |
| DATED | : May 15, 2007 |
| INVENTOR(S) | : David K. Cinader, Jr. |

It is certified that error appears in the above-identified patent and that said Letters Patent is hereby corrected as shown below:

Column 21
Line 34, In Claim 14, delete "500 $^2$/g" and insert -- 500 $m^2/g$ --, therefor.

Signed and Sealed this

Thirty-first Day of July, 2007

JON W. DUDAS
*Director of the United States Patent and Trademark Office*